United States Patent
Lee

(10) Patent No.: US 12,205,689 B2
(45) Date of Patent: Jan. 21, 2025

(54) DENTAL MEDICAL RECORD DEVICE AND DENTAL MEDICAL RECORD METHOD THEREOF

(71) Applicant: THE CATHOLIC UNIVERSITY OF KOREA INDUSTRY-ACADEMIC COOPERATION FOUNDATION, Seoul (KR)

(72) Inventor: Sang Hwa Lee, Seoul (KR)

(73) Assignee: THE CATHOLIC UNIVERSITY OF KOREA INDUSTRY—ACADEMIC COOPERATION FOUNDATION, Seoul (KR)

(*) Notice: Subject to any disclaimer, the term of this patent is extended or adjusted under 35 U.S.C. 154(b) by 253 days.

(21) Appl. No.: 17/792,271

(22) PCT Filed: Jan. 7, 2021

(86) PCT No.: PCT/KR2021/000217
§ 371 (c)(1),
(2) Date: Jul. 12, 2022

(87) PCT Pub. No.: WO2021/145607
PCT Pub. Date: Jul. 22, 2021

(65) Prior Publication Data
US 2023/0039451 A1  Feb. 9, 2023

(30) Foreign Application Priority Data

Jan. 13, 2020 (KR) .................. 10-2020-0004128
Dec. 24, 2020 (KR) .................. 10-2020-0182812

(51) Int. Cl.
*G16H 10/60* (2018.01)
*G06T 7/00* (2017.01)
(Continued)

(52) U.S. Cl.
CPC ........... *G16H 10/60* (2018.01); *G06T 7/0012* (2013.01); *G06V 10/40* (2022.01); *G16H 30/40* (2018.01);
(Continued)

(58) Field of Classification Search
CPC ........ G16H 10/60; G16H 30/40; G06V 10/40; G06T 7/0012; G06T 2207/20081; G06T 2207/20084; G06T 2207/30036
See application file for complete search history.

(56) References Cited

U.S. PATENT DOCUMENTS 6,099,314 A * 8/2000 Kopelman .......... A61C 9/0053
   433/213
6,334,772 B1 * 1/2002 Taub .................... A61C 9/0053
   433/29
(Continued)

FOREIGN PATENT DOCUMENTS

JP       2009226096 A    10/2009
KR    1020190053446 A    5/2019
(Continued)

OTHER PUBLICATIONS

International Search Report (English and Korean) and Written Opinion of the ISA (Korean) issued in PCT/KR2021/000217, mailed Apr. 26, 2021; ISA/KR.
(Continued)

*Primary Examiner* — Michael I Ezewoko
(74) *Attorney, Agent, or Firm* — Harness, Dickey & Pierce, P.L.C.

(57) ABSTRACT

A dental medical record device and a dental medical record method, in which: an image, such as a panoramic photo, a scan image, and a camera image of a patient's oral cavity, is received via artificial intelligence, and charting is performed using the artificial intelligence; and medical records for a (Continued)

treatment area can be read in association with a chart by clicking the treatment area in the image.

9 Claims, 16 Drawing Sheets

(51) Int. Cl.
  *G06V 10/40* (2022.01)
  *G16H 30/40* (2018.01)

(52) U.S. Cl.
  CPC ........... *G06T 2207/20081* (2013.01); *G06T 2207/20084* (2013.01); *G06T 2207/30036* (2013.01)

(56) References Cited

U.S. PATENT DOCUMENTS

| | | | | |
|---|---|---|---|---|
| 6,334,853 B1* | 1/2002 | Kopelman | ............ | A61C 19/05 600/587 |
| 6,463,344 B1* | 10/2002 | Pavloskaia | ............ | G16H 50/50 700/118 |
| 6,542,249 B1* | 4/2003 | Kofman | ............ | G01B 11/2513 356/601 |
| 6,633,789 B1* | 10/2003 | Nikolskiy | ............ | B33Y 50/00 700/118 |
| 6,664,986 B1* | 12/2003 | Kopelman | ............ | A61C 9/0046 715/848 |
| 6,697,164 B1* | 2/2004 | Babayoff | ............ | G01B 11/24 356/601 |
| 6,845,175 B2* | 1/2005 | Kopelman | ............ | A61B 6/51 382/294 |
| 6,979,196 B2* | 12/2005 | Nikolskiy | ............ | A61C 19/05 433/214 |
| 7,030,383 B2* | 4/2006 | Babayoff | ............ | G03H 1/32 250/370.08 |
| 7,202,466 B2* | 4/2007 | Babayoff | ............ | G02B 27/0933 359/368 |
| 7,255,558 B2* | 8/2007 | Babayoff | ............ | A61C 17/022 433/29 |
| 7,286,954 B2* | 10/2007 | Kopelman | ............ | G16Z 99/00 700/118 |
| 7,319,529 B2* | 1/2008 | Babayoff | ............ | G01J 3/02 348/E13.005 |
| 7,373,286 B2* | 5/2008 | Nikolskiy | ............ | G06T 17/00 703/2 |
| 7,507,088 B2* | 3/2009 | Taub | ............ | A61C 7/146 433/24 |
| 7,545,372 B2* | 6/2009 | Kopelman | ............ | A61C 13/0004 433/213 |
| 7,698,068 B2* | 4/2010 | Babayoff | ............ | G01J 3/0205 702/19 |
| 7,916,911 B2* | 3/2011 | Kaza | ............ | A61C 9/0046 382/128 |
| 8,108,189 B2* | 1/2012 | Chelnokov | ............ | A61C 7/002 433/213 |
| 8,165,213 B2* | 4/2012 | Ha | ............ | H04N 7/0112 375/240.2 |
| 8,244,028 B2* | 8/2012 | Kuo | ............ | G06T 7/33 382/128 |
| 8,582,878 B1* | 11/2013 | Tzur | ............ | H04N 23/86 382/167 |
| 8,587,582 B2* | 11/2013 | Matov | ............ | A61C 7/00 345/420 |
| 8,948,482 B2* | 2/2015 | Levin | ............ | A61B 6/512 382/128 |
| D742,518 S * | 11/2015 | Barak | ............ | D24/176 |
| 9,192,305 B2* | 11/2015 | Levin | ............ | A61B 5/0088 |
| 9,261,356 B2* | 2/2016 | Lampert | ............ | G02B 3/0056 |
| 9,261,358 B2* | 2/2016 | Atiya | ............ | A61B 1/0605 |
| 9,299,192 B2* | 3/2016 | Kopelman | ............ | A61C 13/0004 |
| D760,901 S * | 7/2016 | Barak | ............ | D24/158 |
| 9,393,087 B2* | 7/2016 | Moalem | ............ | A61C 1/088 |
| 9,408,679 B2* | 8/2016 | Kopelman | ............ | A61C 11/00 |
| 9,431,887 B2* | 8/2016 | Boltanski | ............ | H02K 41/0356 |
| 9,439,568 B2* | 9/2016 | Atiya | ............ | G01B 11/30 |
| 9,451,873 B1* | 9/2016 | Kopelman | ............ | G06T 7/13 |
| D768,861 S * | 10/2016 | Barak | ............ | D24/176 |
| D771,817 S * | 11/2016 | Barak | ............ | D24/176 |
| 9,482,939 B2* | 11/2016 | Moon | ............ | G03B 37/04 |
| 9,491,863 B2* | 11/2016 | Boltanski | ............ | G02B 27/123 |
| D774,193 S * | 12/2016 | Makmel | ............ | A61C 9/0053 D24/152 |
| 9,510,757 B2* | 12/2016 | Kopelman | ............ | A61B 5/4552 |
| 9,660,418 B2* | 5/2017 | Atiya | ............ | G01B 11/0608 |
| 9,668,829 B2* | 6/2017 | Kopelman | ............ | A61B 90/90 |
| 9,675,430 B2* | 6/2017 | Verker | ............ | G02B 23/2446 |
| 9,693,839 B2* | 7/2017 | Atiya | ............ | A61C 9/0066 |
| 9,717,402 B2* | 8/2017 | Lampert | ............ | A61C 9/0066 |
| 9,724,177 B2* | 8/2017 | Levin | ............ | A61C 9/0053 |
| 9,844,426 B2* | 12/2017 | Atiya | ............ | A61C 9/006 |
| 10,076,389 B2* | 9/2018 | Wu | ............ | A61C 7/002 |
| 10,098,714 B2* | 10/2018 | Kuo | ............ | A61C 7/002 |
| 10,108,269 B2* | 10/2018 | Sabina | ............ | A61C 5/77 |
| 10,111,581 B2* | 10/2018 | Makmel | ............ | A61B 1/00163 |
| 10,111,714 B2* | 10/2018 | Kopelman | ............ | G06T 7/593 |
| 10,123,706 B2* | 11/2018 | Elbaz | ............ | G06T 17/00 |
| 10,136,972 B2* | 11/2018 | Sabina | ............ | A61B 6/51 |
| 10,251,732 B2* | 4/2019 | Lee | ............ | A61C 13/0004 |
| 10,380,212 B2* | 8/2019 | Elbaz | ............ | G06T 17/00 |
| 10,390,913 B2* | 8/2019 | Sabina | ............ | A61B 6/512 |
| 10,453,269 B2* | 10/2019 | Furst | ............ | A61B 8/5261 |
| 10,456,043 B2* | 10/2019 | Atiya | ............ | A61C 7/002 |
| 10,499,793 B2* | 12/2019 | Ozerov | ............ | A61B 1/00016 |
| 10,504,386 B2* | 12/2019 | Levin | ............ | G06T 1/0007 |
| 10,507,087 B2* | 12/2019 | Elbaz | ............ | A61B 1/00016 |
| 10,517,482 B2* | 12/2019 | Sato | ............ | A61C 7/002 |
| 10,695,150 B2* | 6/2020 | Kopelman | ............ | A61C 1/082 |
| 10,708,574 B2* | 7/2020 | Furst | ............ | A61B 1/00096 |
| 10,726,301 B2* | 7/2020 | Joyce | ............ | G06N 20/00 |
| 10,772,506 B2* | 9/2020 | Atiya | ............ | G01B 11/24 |
| 10,806,766 B2* | 10/2020 | Lee | ............ | A61K 36/488 |
| 10,813,727 B2* | 10/2020 | Sabina | ............ | A61C 7/002 |
| 10,888,399 B2* | 1/2021 | Kopelman | ............ | G06V 40/171 |
| 10,952,816 B2* | 3/2021 | Kopelman | ............ | A61C 1/082 |
| 10,980,613 B2* | 4/2021 | Shanjani | ............ | G02B 27/0172 |
| 11,013,581 B2* | 5/2021 | Sabina | ............ | A61B 6/512 |
| 11,096,765 B2* | 8/2021 | Atiya | ............ | G02B 27/4222 |
| 11,151,421 B2* | 10/2021 | Joyce | ............ | G06F 18/24 |
| 11,154,311 B2* | 10/2021 | Lee | ............ | A61B 17/151 |
| 11,494,899 B2* | 11/2022 | Joyce | ............ | B26B 21/4056 |
| 11,565,513 B2* | 1/2023 | Lee | ............ | B32B 27/34 |
| 11,752,650 B2* | 9/2023 | Joyce | ............ | G16H 50/20 700/275 |
| 11,759,295 B2* | 9/2023 | Sabina | ............ | A61B 5/0086 348/66 |
| 11,819,223 B2* | 11/2023 | Lee | ............ | A61B 17/15 |
| 11,865,007 B2* | 1/2024 | Lee | ............ | A61F 2/3099 |
| 2003/0065523 A1* | 4/2003 | Pruche | ............ | A61B 5/0088 382/118 |
| 2006/0239526 A1* | 10/2006 | Jonusauskas | ............ | A61B 5/0088 348/66 |
| 2010/0141931 A1* | 6/2010 | Ramirez Mancilla | ............ | G01J 3/50 356/402 |
| 2011/0069149 A1* | 3/2011 | Park | ............ | G06V 10/20 348/36 |
| 2012/0015316 A1* | 1/2012 | Sachdeva | ............ | A61B 1/24 382/128 |
| 2014/0051040 A1* | 2/2014 | Kilcher | ............ | A61C 19/003 433/226 |
| 2014/0267593 A1* | 9/2014 | Kim | ............ | H04N 23/698 348/36 |
| 2014/0314291 A1* | 10/2014 | Souza | ............ | G06T 7/0012 382/131 |
| 2015/0057622 A1* | 2/2015 | Hyde | ............ | G06F 16/2455 604/289 |
| 2016/0331465 A1* | 11/2016 | Kim | ............ | A61B 5/4585 |
| 2017/0007374 A1* | 1/2017 | Lee | ............ | A61C 13/0019 |
| 2017/0035601 A1* | 2/2017 | Lee | ............ | A61F 5/566 |
| 2017/0151039 A1* | 6/2017 | Lee | ............ | A61C 19/06 |
| 2017/0157858 A1* | 6/2017 | Lee | ............ | B29C 64/386 |

(56) References Cited

U.S. PATENT DOCUMENTS

| | | | |
|---|---|---|---|
| 2019/0029784 A1* | 1/2019 | Moalem | A61C 13/0004 |
| 2019/0105842 A1* | 4/2019 | Dau | B33Y 50/00 |
| 2019/0175314 A1* | 6/2019 | Lagardere | A61C 9/0053 |
| 2019/0254787 A1* | 8/2019 | Lee | A61C 13/08 |
| 2019/0313963 A1* | 10/2019 | Hillen | G06V 10/764 |
| 2019/0388103 A1* | 12/2019 | Lee | B33Y 80/00 |
| 2019/0388193 A1* | 12/2019 | Saphier | A61C 9/0066 |
| 2020/0281700 A1* | 9/2020 | Kopelman | A61B 1/24 |
| 2020/0281702 A1* | 9/2020 | Kopelman | G06N 20/00 |
| 2020/0306142 A1* | 10/2020 | Mo | A61K 6/56 |
| 2020/0315434 A1* | 10/2020 | Kopelman | A61B 1/00103 |
| 2020/0349698 A1* | 11/2020 | Minchenkov | G06T 17/00 |
| 2020/0349705 A1* | 11/2020 | Minchenkov | A61C 13/0004 |
| 2020/0372677 A1* | 11/2020 | Yoon | G06V 40/193 |
| 2020/0404243 A1* | 12/2020 | Saphier | A61C 9/006 |
| 2021/0030503 A1* | 2/2021 | Shalev | A61C 9/0053 |
| 2021/0059796 A1* | 3/2021 | Weiss | A61C 9/0053 |
| 2021/0068773 A1* | 3/2021 | Moshe | A61B 6/51 |
| 2022/0142782 A1* | 5/2022 | Lee | A61F 2/30942 |
| 2023/0039451 A1* | 2/2023 | Lee | G16H 40/20 |
| 2023/0211612 A1* | 7/2023 | Yoon | B41J 2/17513<br>347/86 |
| 2023/0250224 A1* | 8/2023 | Park | C08F 220/325<br>524/605 |
| 2023/0268482 A1* | 8/2023 | Lee | F26B 21/12<br>34/337 |

FOREIGN PATENT DOCUMENTS

| | | |
|---|---|---|
| KR | 102015224 B1 | 10/2019 |
| KR | 1020190129247 A | 11/2019 |
| KR | 1020190142687 A | 12/2019 |

OTHER PUBLICATIONS

Korean Office Action issued in KR1020200182812, dated Sep. 28, 2021.

* cited by examiner text chart(140)

16 secondary caries
44 periapical lesion
Old AM: #47, 46, 37 #47
attrition #41,42,43

& symbol chart(142)

guide sample

FIG. 8B

```
증상 : 치아
Pain Scale : NRS
S&O placed implants immediately after #45, 44 extracted under local anesthesia
    placed implants based on the height of the lingual and mesial alveolar tip.
    removed the remaining buccal tip, transplanted to the implant crestal adjacent
    to the tooth extraction mesiodistal distance is about 12mm.
    Failed to place two implant so placed one molar-shape implant A
    - primary    Simplex periodontitis
    - ancillary  Temporomandibular joint disorders
    - ancillary  Teeth-grinding
    - ancillary  Loss of teeth due to accident, extraction or local periodontal disease
P
    NEXT) Dressing
```

DENTAL MEDICAL RECORD DEVICE AND DENTAL MEDICAL RECORD METHOD THEREOF

CROSS-REFERENCE TO RELATED APPLICATIONS

This application is a U.S. National Phase Application under 35 U.S.C. 371 of International Application No. PCT/KR2021/000217, filed on Jan. 7, 2021, which claims the benefit of Korean Patent Application No. 10-2020-0004128, filed on Jan. 13, 2020, and Korean Patent Application No. 10-2020-0182812, filed on Dec. 24, 2020. The entire disclosures of the above applications are herein incorporated by reference in their entireties. The present patent application claims priority to other applications to be filed in other countries, the disclosures of which are also incorporated by reference herein in their entireties.

TECHNICAL FIELD

The present invention provides a dental medical record device for creating a dental medical record and a dental medical record method thereof.

BACKGROUND ART

During dental treatment, to create a dental medical record, a doctor looks at the panoramic photo captured around a patient's teeth and performs an overall basic charting. Further, the doctor adds the data obtained during the oral examination by the patient to the dental medical record. After evaluating the patient's teeth, the doctor marks the dental medical record with text or symbols.

In this case, the doctor must evaluate each of the multiple teeth. Due to possible infection issues between the time of examination and the time of recording, instead of looking at the patient and filling out the dental medical record, the doctor dictates to an assistant doctor to allow the assistant doctor to record, or an assistant dictates and the doctor transcribes the dental medical record. Further, in order to review the treatment history for each of multiple teeth, the doctor should separately search for the medical record and receipt history for each tooth.

Currently, it thus takes a long time to create a dental medical record during dental treatment, and errors may occur while the assistant doctor transcribes when writing a dental medical record. Further, there is a problem in that it is difficult to dictate and record immediately when charting in a hospital or private clinic without a specialist.

DETAILED DESCRIPTION OF THE INVENTION

Technical Problem

Embodiments provide a dental medical record device and a dental medical record method capable of reducing the time and costs required for creating a dental medical record.

Embodiments also provide a dental medical record device and a dental medical record method capable of enhancing the accuracy of prognosis and reducing the possibility of cross-infection of patients.

Embodiments also provide a dental medical record device and a dental medical record method capable of easily creating, storing, and viewing dental medical records.

However, the objects of the embodiments are not limited thereto, and other objects may also be present.

Technical Solution

The disclosure provides a dental medical record device and a dental medical record method that receive an image, such as a panoramic photo, a scan image, and a camera image, for a patient's oral cavity through artificial intelligence, perform charting using artificial intelligence, and if the treatment site is clicked in the corresponding image, allows the medical records for the treatment site in association with the chart.

In an aspect, a dental medical record method according to an embodiment comprises reading an image for a patient's oral cavity to mark the patient's oral cavity condition on a prognosis chart, using a text format, symbols, or both text and symbols and displaying the image and the prognosis chart.

In another aspect, a dental medical record device according to another embodiment comprises an input unit receiving an image for a patient's oral cavity, a controller reading the image for the patient's oral cavity to determine the patient's oral cavity condition and marking the patient's oral cavity condition on a prognosis chart, using a text format, symbols, or both text and symbols and an output unit displaying the image and the prognosis chart.

In another aspect, a non-transitory computer-readable storage medium according to another embodiment stores instructions, when executed by one or more processors, instructions that, when executed by one or more processors, enable the one or more processors to perform a dental medical record method.

When executed by the one or more processors, the instructions enable the computer device to read an image for a patient's oral cavity to mark the patient's oral cavity condition on a prognosis chart, using a text format, symbols, or both text and symbols and display the image and the prognosis chart.

Advantageous Effects

By the dental medical record device and the dental medical record method according to embodiments, it is possible to reduce the time and costs required for creating a dental medical record.

By the dental medical record device and the dental medical record method according to embodiments, it is also possible to enhance the accuracy of prognosis and reduce the possibility of cross-infection of patients.

By the dental medical record device and the dental medical record method according to embodiments, a dental medical record device and a dental medical record method capable of easily creating, storing, and viewing dental medical records are provided.

BRIEF DESCRIPTION OF THE DRAWINGS

FIGS. 8A and 8B are an example of viewing information about a treatment site in a pop-up;

DETAILED DESCRIPTION OF THE INVENTION

Hereinafter, exemplary embodiments of the inventive concept will be described in detail with reference to the accompanying drawings. The inventive concept, however, may be modified in various different ways, and should not be construed as limited to the embodiments set forth herein. Like reference denotations may be used to refer to the same or similar elements throughout the specification and the drawings. However, the present invention may be implemented in other various forms and is not limited to the embodiments set forth herein. For clarity of the disclosure, irrelevant parts are removed from the drawings, and similar reference denotations are used to refer to similar elements throughout the specification.

In embodiments of the present invention, when an element is "connected" with another element, the element may be "directly connected" with the other element, or the element may be "electrically connected" with the other element via an intervening element. When an element "comprises" or "includes" another element, the element may further include, but rather than excluding, the other element, and the terms "comprise" and "include" should be appreciated as not excluding the possibility of presence or adding one or more features, numbers, steps, operations, elements, parts, or combinations thereof.

When the measurement of an element is modified by the term "about" or "substantially," if a production or material tolerance is provided for the element, the term "about" or "substantially" is used to indicate that the element has the same or a close value to the measurement and is used for a better understanding of the present invention or for preventing any unscrupulous infringement of the disclosure where the exact or absolute numbers are mentioned. As used herein, "step of" A or "step A-ing" does not necessarily mean that the step is one for A.

As used herein, the term "part" may mean a unit or device implemented in hardware, software, or a combination thereof. One unit may be implemented with two or more hardware devices or components, or two or more units may be implemented in a single hardware device or component.

As used herein, some of the operations or functions described to be performed by a terminal or device may be, instead of the terminal or device, performed by a server connected with the terminal or device. Likewise, some of the operations or functions described to be performed by a server may be performed by a terminal or device connected with the server, instead of the server.

As used herein, some of the operations or functions described to be mapped or matched with a terminal may be interpreted as mapping or matching the unique number of the terminal, which is identification information about the terminal, or personal identification information.

Hereinafter, embodiments of the disclosure are described in detail with reference to the accompanying drawings.

Figure 1:
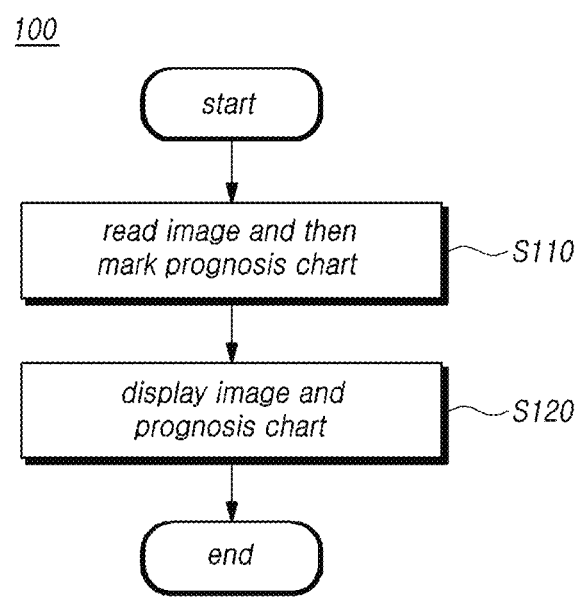
FIG. 1 is a flowchart of a dental medical record method according to an embodiment.

FIG. 1 is a flowchart of a dental medical record method according to an embodiment.

Referring to FIG. 1, a dental medical record method 100 according to an embodiment includes the step S110 of reading an image for a patient's oral cavity and marking a prognosis chart with text or a symbol or in a combination of text and a symbol for the patient's oral cavity condition and the step S120 of displaying the image and the prognosis chart.

The image may be one of a panoramic photo, a scan image, or a camera image obtained by one or two or more of radiography, oral camera, scanning device, and occlusion check data for the patient's oral cavity, as is described below with reference to FIG. 2.

Further, the patient's oral cavity condition may be at least one of the dental formula, dental conditions, or surrounding structures of the teeth.

In the step S110 of marking the prognosis chart, artificial intelligence is continuously trained with continuously collected training images and accumulated chart data so that artificial intelligence reads the images, as described below with reference to FIG. 11. As in the above-described drawings, e.g., as shown in FIGS. 7C and 7D described below, artificial intelligence may be trained with training images including, e.g., a guide chip or a guide sample. As such, since the image including the guide chip or guide sample is obtained in the process of pre-treating the training image or obtaining the image, it is possible to enhance the training effect and the accuracy of determination in the prognosis chart marking step S110.

Artificial intelligence may automatically learn the features for input values by being trained with a large amount of data from a deep neural network composed of a multi-layered network, and train the multi-layered network to minimize errors in prediction accuracy and read images.

As described below with reference to FIGS. 8 to 10, in the step S120 of displaying the image and chart, if a specific treatment site of the image is selected, information about the treatment site is displayed, and if the image of the treatment site is selected, a treatment summary memo window is displayed, and if the treatment summary memo window is selected, a chart for the treatment site is output.

Figure 2:
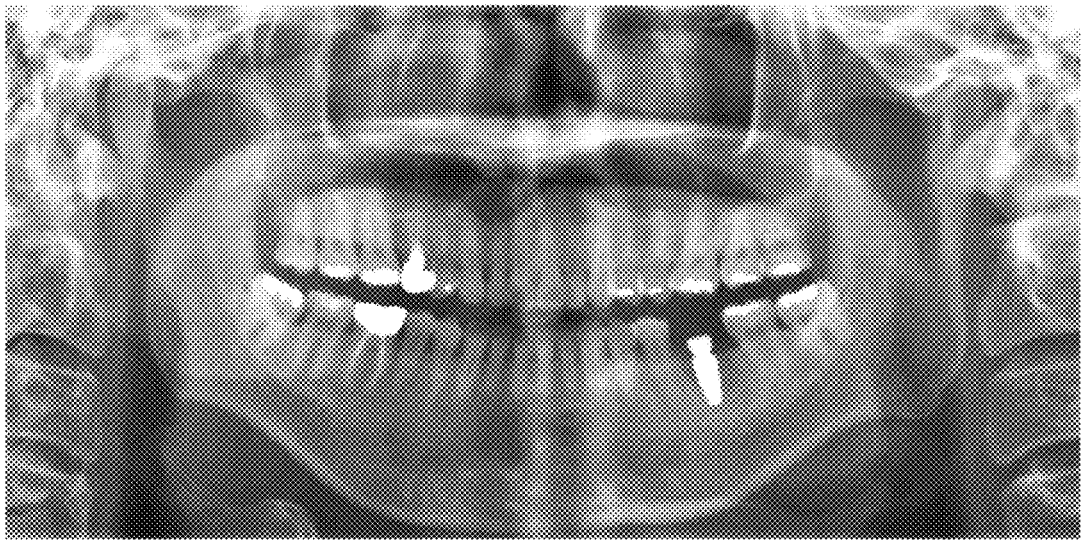
FIG. 2 is an example of an image captured for a patient's oral cavity.

FIG. 2 is an example of an image captured by the patient's oral cavity. FIG. 2 is a panoramic photo captured for the patient's oral cavity, illustrating the patient's oral cavity condition.

Referring to FIGS. 1 and 2, the dental medical record method 100 according to an embodiment may, in the step S110 of marking the prognosis chart, read information about the dental formula, teeth conditions (e.g., periodontal conditions (gum conditions), dental caries, tooth loss, restoration, prosthetics, implants, wisdom teeth), and surrounding structures of the teeth (e.g., temporomandibular joint) based on the image, such as the panoramic photo of FIG. 2.

According to an embodiment, the dental medical record method 100 may read images, such as panoramic photos, scan images or camera images for the oral cavity, and move the results to an electronic medical record (EMR) chart, thereby obtaining a prognosis effect.

Figure 3:
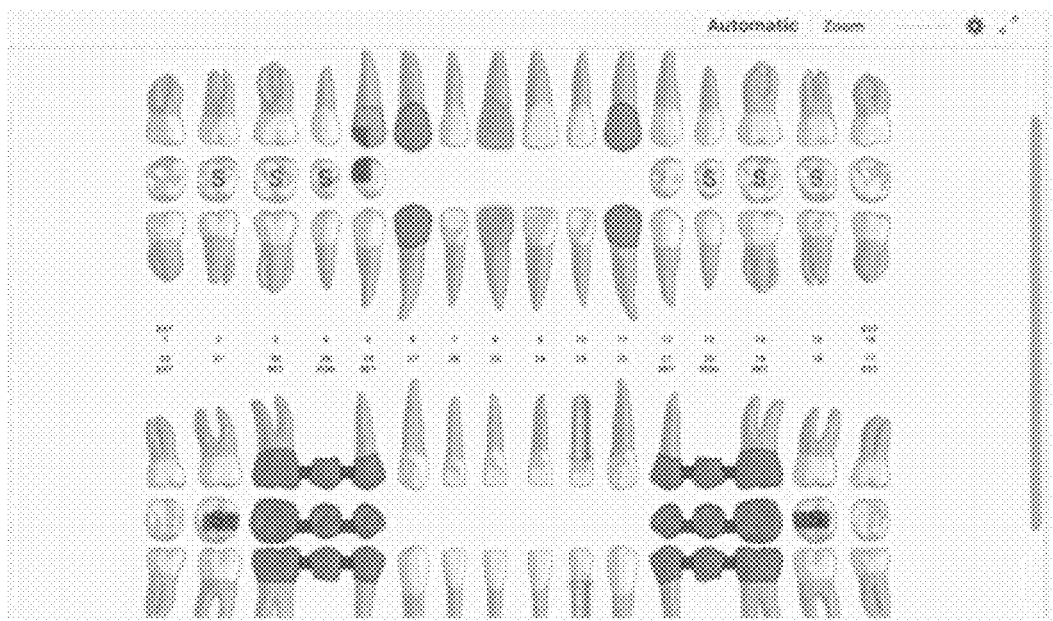
FIG. 3 is an example of an EMR chart.

FIG. 3 is an example of an EMR chart. The EMR chart of FIG. 3 is a symbol chart composed of teeth-related symbols.

Referring to FIGS. 1 and 3, the dental medical record method 100 according to an embodiment may, in the step S110 of marking the prognosis chart, read the images, such as panoramic photos, scan images or camera images for the oral cavity, determining whether the patient's oral cavity condition is normal or whether there is a disease in the teeth, alveolar bone, and jaw bone. Such images may be obtained by means of radiography, oral camera, scanning device, occlusion check data, and the like.

Further, the dental medical record device may display the content read through the above-described images, in the format of text, symbols, or in a combination of text and symbols.

Figure 4:
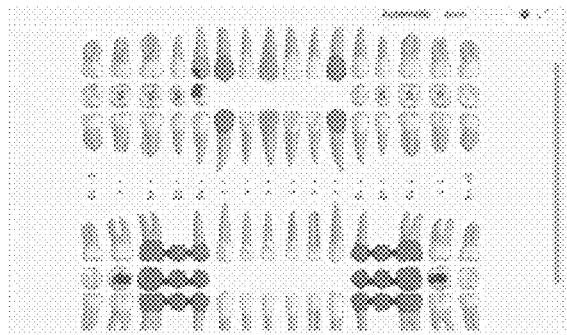
FIG. 4 is an example illustrating a text and symbol chart.

FIG. 4 is an example illustrating a text and symbol chart.

Referring to FIG. 4, the text chart 140 is a prognosis chart in which the content read through the images is depicted in narrative text in the step S110 of marking the prognosis chart.

For example, the text chart 140 may represent information indicating that tooth #16 has secondary caries, tooth #44 has a periapical lesion, teeth #41, 42, and 43 have attrition, and teeth #47, 46, and 37 have Old AM.

The symbol chart 142 is a chart in which the content read through the images is depicted through various symbols. For example, the symbol chart may depict tooth loss, periodontal disease, dental caries, restoration, and the like, based on standard symbol standards.

The dental medical record method 100 according to an embodiment may read the images through artificial intelligence using a machine learning model, a deep learning model, etc., as is described below with reference to FIG. 10. The artificial intelligence used in the dental medical record device may learn the diseases that occur in teeth, alveolar bones, and jaw bones.

In this case, the artificial intelligence may set a dividing criterion while inputting video data for normal structures and lesions in the oral cavity during the learning process.

As an example, when the alveolar bone is positioned up to 1 mm below the area where the crown and the root meet, the alveolar bone may be recognized as normal. As another example, if there is no tooth in the alveolar bone, it may be recognized as tooth loss.

Meanwhile, the diagnosis of lesions using artificial intelligence may be performed based on factors, such as tooth color, tooth loss, and radiography information in the images (e.g., houndsfield scale).

The dental medical record method 100 according to an embodiment may continuously train the artificial intelligence with continuously collected training images and accumulated chart data, thereby increasing the accuracy for the artificial intelligence to read the images.

Further, the dental medical record method 100 according to an embodiment may, after reading the images through the artificial intelligence, chart the same and associate the images with the patient's treatment and receipt content, in the step S110 of marking the prognosis chart. For example, if the doctor clicks on the image, a pop-up 144 indicating information about the treatment date for the clicked area and the receipt memo window may be generated. Further, if the doctor clicks the receipt memo window on the pop-up 144, information about the chart associated with the corresponding memo window may be accessed.

Figure 5:
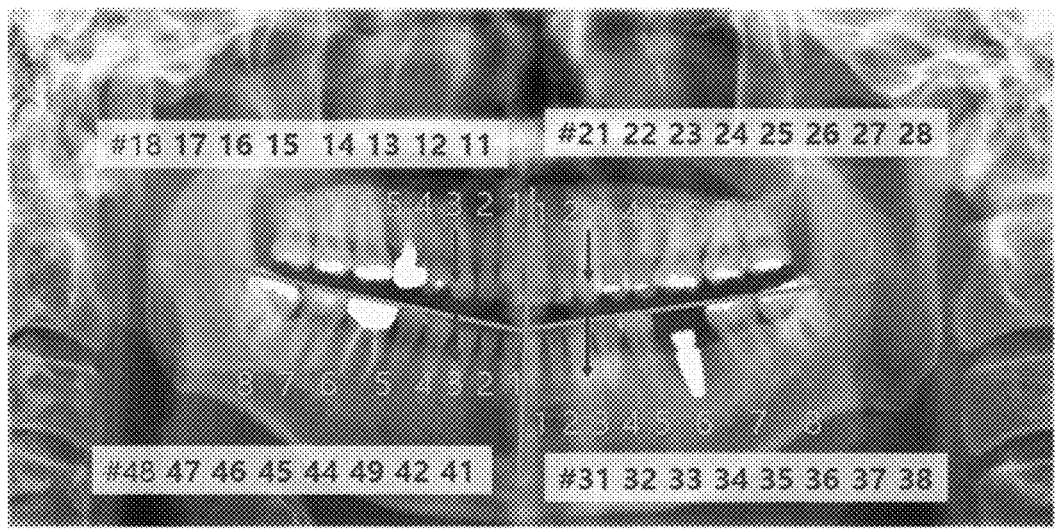
FIG. 5 is an example of a photo illustrating a patient's teeth and dental formula.

FIG. 5 is an example of a photo illustrating a patient's teeth and dental formula.

Referring to FIG. 5, the dental formula is a scheme for distinguishing the teeth and divides the left, right, top, and bottom (1 to 8) of the center of the patient's oral cavity and distinguishes incisors and molars with respect to canine teeth.

The roots of the teeth are positioned inside the bone (#11 to #48), the crown is positioned outside the bone. The teeth are nearly perpendicular to the bone.

Figure 6:
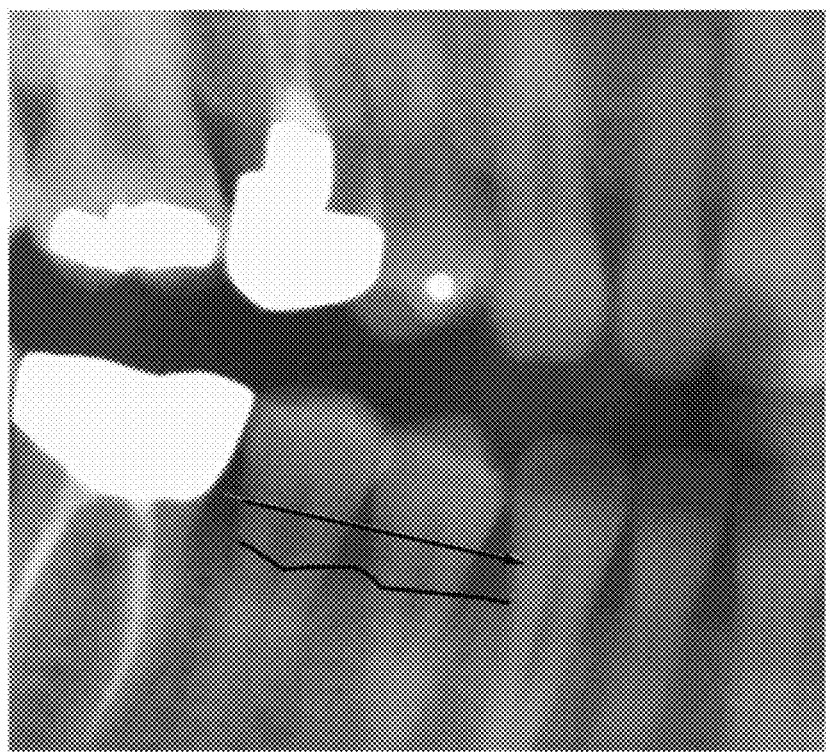
FIG. 6 is an example of a photo illustrating a patient's periodontal condition.

FIG. 6 is an example of a photo illustrating a patient's periodontal condition.

The dental medical record method 100 according to an embodiment may determine that it is normal if the alveolar bone is positioned up to 1 mm in the root direction from the site (arrow) where the crown and the root of the tooth meet and that it is an alveolar bone loss if the alveolar bone is positioned therebelow. Alveolar bone loss includes horizontal loss and vertical loss. Further, the dental medical record method 100 according to an embodiment may identify the state of the furcation, which is the site where the root of the molar is split.

The dental medical record method 100 according to an embodiment determines the patient's periodontal condition of alveolar bone loss after reading the image shown in FIG. 6 through artificial intelligence in the step S110 of marking the prognosis chart.

Figure 7A:
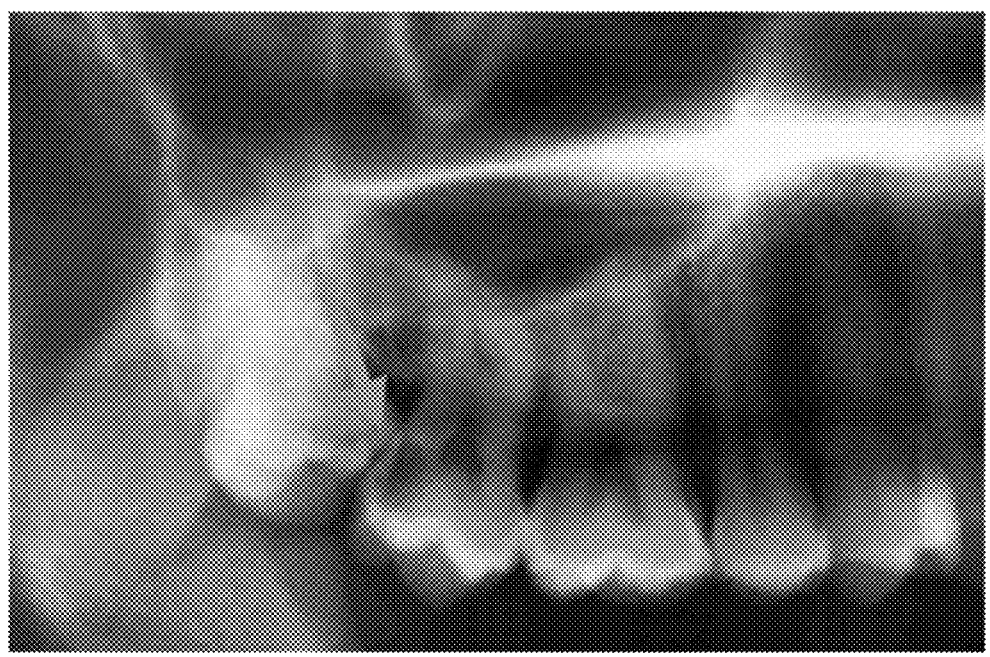
FIGS. 7A and 7B are examples of photos illustrating a patient's dental caries and restoration state.
Figure 7B:
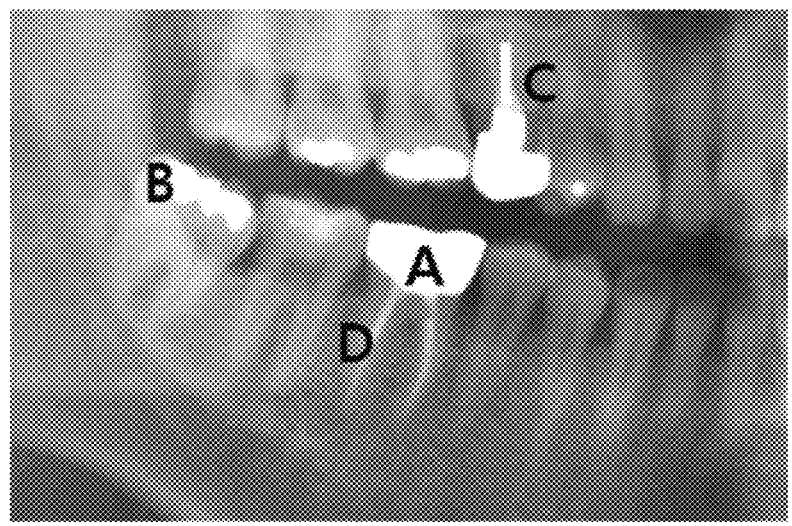
Figure 7C:
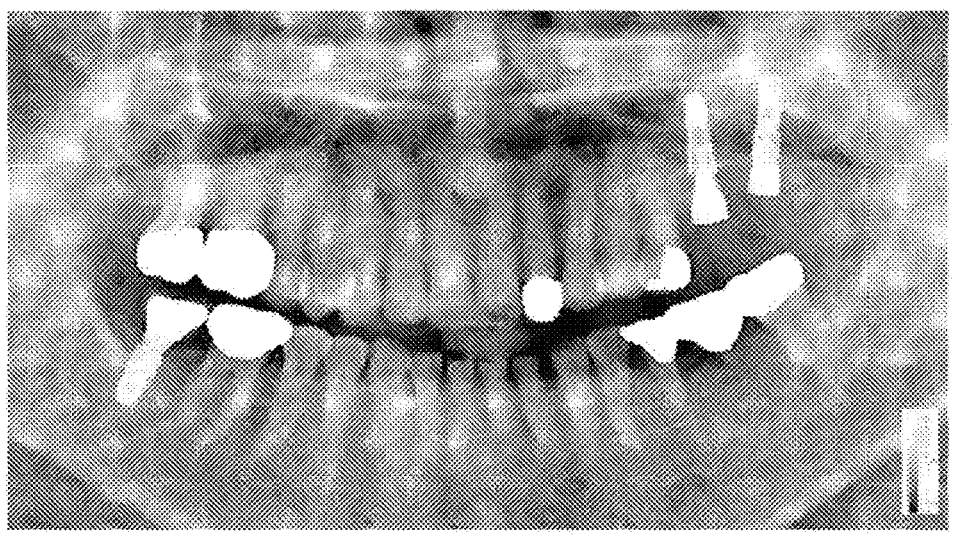
FIGS. 7C and 7D are training images of a guide chip and a guide sample.
Figure 7D:
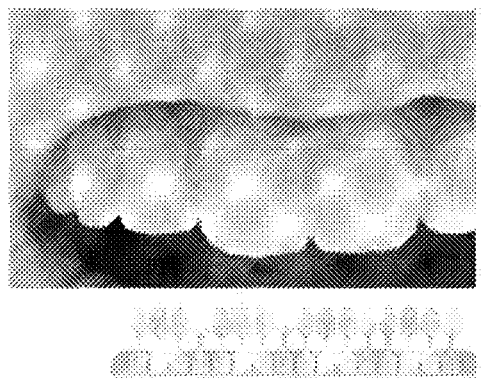

FIGS. 7A and 7B are examples of photos illustrating a patient's dental caries and restoration state.

As shown in FIG. 7A, dental caries means a defect in enamel, dentin, or pulp included in the tooth.

The dental medical record method 100 according to an embodiment determines the patient's periodontal condition of dental caries after reading the image shown in FIG. 7A through artificial intelligence in the step S110 of marking the prognosis chart.

As shown in FIG. 7B, among the dental restorations, crown A does not transmit the radiation throughout the entire crown and, among the dental restorations, inlay or amalgam B does not transmit the radiation for a portion of the crown. Among the dental restorations, post C is shown by a dark white straight line within the root of the tooth. The tooth D that has undergone root canal treatment is shown by a white curve along the root line at the center of the root of the tooth.

The dental medical record method 100 according to an embodiment reads the image shown in FIG. 7B through artificial intelligence, marks crown in position A, inlay or amalgam in position B, post in position C, and root canal in position D in the step S110 of marking the prognosis chart.

FIG. 7C is an example of a panoramic image including a guide chip, captured by a panoramic image capture device.

The panoramic image capture device positions a capture subject, e.g., a patient, on a cylindrical body equipped with an X-ray source, and then rotates the X-ray source and panoramic image detector around the patient, thereby obtaining a plurality of images. The panoramic image capture device naturally connects these images to obtain a panoramic image as shown in FIG. 7C. When capturing the panoramic image, guide chips having different gray scales (e.g., houndsfield unit (HU)) are mounted on the panorama detector to obtain a panoramic image including a guide chip as shown in FIG. 7C.

The artificial intelligence may be trained with the training images including guide chips.

Since the artificial intelligence is trained with the guide sample-containing training images, the patient's periodontal condition, such as dental caries, is more accurately determined after reading the images through the artificial intelligence in the step S110 of marking the prognosis chart.

In the step S110 of marking the prognosis chart, when the image is read through the trained artificial intelligence, the difference in dental caries and the case in which the transmission of radiations has been reduced, such as enamel, dentin, or pulp, may be more accurately read as compared with the normal tooth tissue in the panoramic image. Further, even when the radiodensity differs in the panoramic image depending on, e.g., the anatomical structure of each patient, the size of the patient, and the posture, it is possible to more accurately read the periodontal condition of dental caries.

In the above-described example, in the step S110 of marking the prognosis chart, the dental caries is determined after reading the image including the guide chip shown in FIG. 7C through artificial intelligence. For the same reason, after reading the image including the guide chip shown in FIG. 7C through artificial intelligence, it is possible to accurately determine periodontal conditions or diagnose other lesions, such as periodontitis, apical lesions, and alveolar bone loss.

FIG. 7D is an example of an image including a guide sample, captured by a camera or a scanner.

When capturing with a camera or scanner, an image including a guide sample is obtained as shown in FIG. 7D. The guide sample includes a color number and a color corresponding to the color number.

The artificial intelligence may be trained with the training images including guide samples. In the image, the tooth color is affected by lighting and shadow, the capture camera. Accordingly, since the artificial intelligence is trained with the guide sample-containing training images, the patient's tooth color may be more accurately determined after reading the images through the artificial intelligence in the step S110 of marking the prognosis chart.

Therefore, in the step S120 of displaying the image and the prognosis chart, if a specific tooth is clicked on the image, the color of the specific tooth, e.g., an optical tooth color, presented by the trained artificial intelligence is indicated with the color number (e.g., N3) and/or color (e.g., yellow) of the guide sample, on the image. Thus, it is possible to suggest the color of the restoration or prosthesis that best matches the color of the patient's teeth, providing an effective, aesthetic treatment method.

Figure 8A:
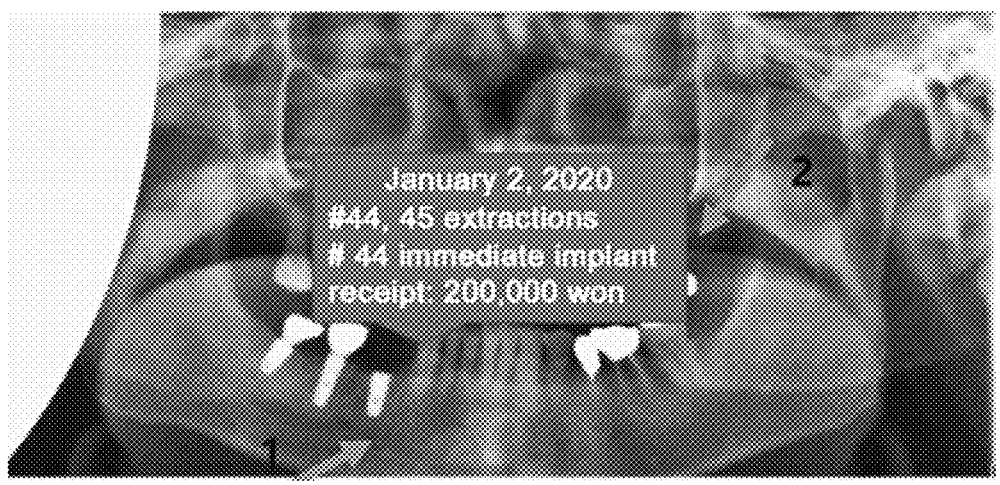

FIGS. 8A and 8B are examples of viewing information about a treatment site in a pop-up.

Referring to FIG. 8A, in the step S120 of displaying the image and the chart, if the doctor clicks on a specific treatment site on the image, information about the treatment site (e.g., treatment title, date, or receipt memo window) is displayed. The image of the treatment site and information about the treatment site may be linked in the form of a hyperlink. For example, as the information about the treatment site, "Jan. 2, 2020 #44, 45 extractions, 44 immediate implants, receipt: 200,000 won" is displayed as shown in FIG. 8A.

Referring to FIG. 8B, if the image of the corresponding treatment site is clicked, a treatment summary memo (e.g., treatment title, date, and receipt) window is displayed, and if the treatment summary memo window is clicked, a chart for the treatment site may be output.

Further, if the receiving memo window is clicked, a chart linked to the receiving memo window may be output.

Figure 9:
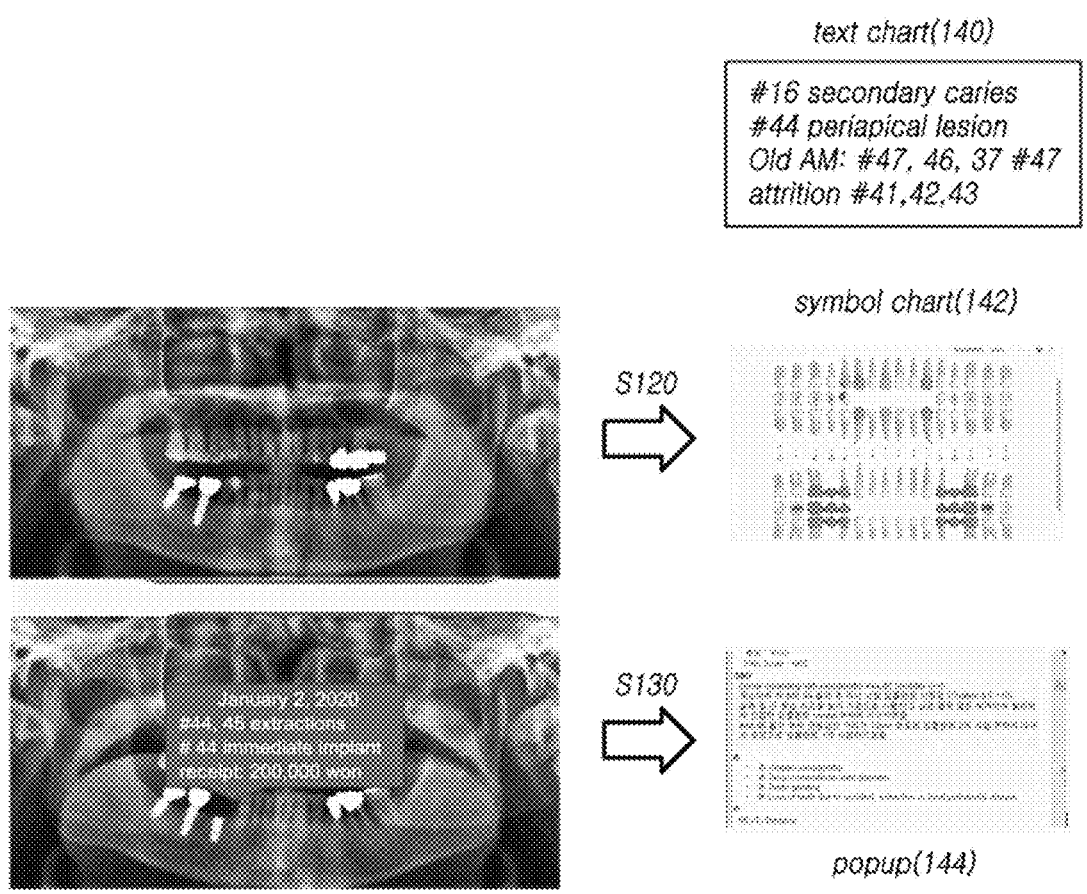
FIGS. 9 and 10 are schematic views illustrating the operation of a dental medical record device.
Figure 10:
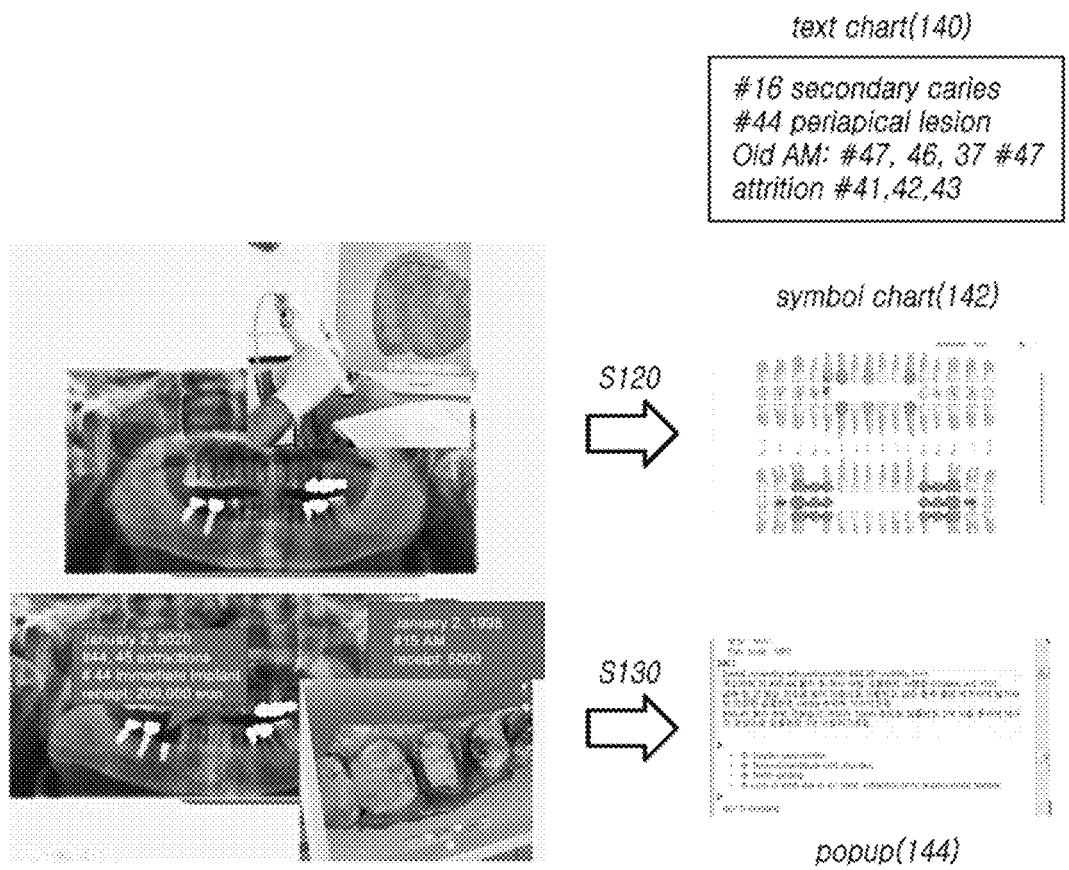

FIGS. 9 and 10 are schematic views illustrating the operation of a dental medical record method according to an embodiment.

Referring to FIGS. 1 and 9 and 10, a dental medical record method 100 according to an embodiment may read an image (e.g., a panoramic photo) of the patient's oral cavity and then create a prognosis chart composed of text or symbols in the step S110 of marking the prognosis chart.

The dental medical record method 100 according to an embodiment may enhance the accuracy of creating the prognosis chart by continuously learning individually input information or accumulated chart records through artificial intelligence using a machine learning model or a deep learning model in the step S110 of marking the prognosis chart.

In the step S120 of displaying the image and the chart, the dental medical record method 100 according to an embodiment may generate a treatment popup 144 including information, such as treatment title, date, and receipt memo window, if the doctor clicks the treatment site on the image (e.g., panoramic photo) for the patient's oral cavity and output a chart linked to the receipt memo window if the doctor clicks the receipt memo window.

By the dental medical record method 100 according to an embodiment, even a hospital or private clinic without a specialist may enhance convenience and accuracy when recording dental medical records. Further, it allows the specialist to focus on studying specialized care rather than dictation. Further, it is possible to increase the accuracy of determining the patient's oral condition based on the accumulated image information and charting data.

Figure 11:
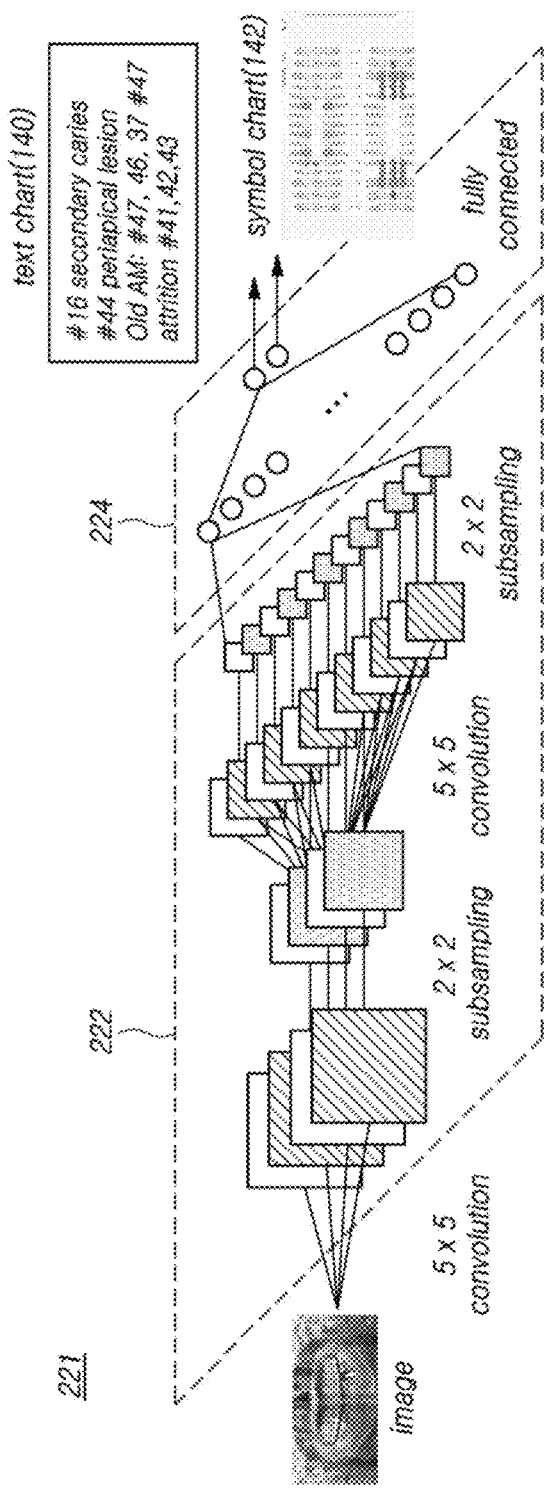
FIG. 11 is a view of a configuration of a deep learning model used in a dental medical record method 100 according to an embodiment of FIG. 1.

FIG. 11 is a view of a configuration of a deep learning model used in a dental medical record method 100 according to an embodiment of FIG. 1.

Referring to FIG. 11, a deep learning model 221 that may be used in the dental medical record method 100 according to an embodiment may be a model in which the artificial neural networks is composed of multiple layers stacked. In other words, the deep learning model is a model in such a form as to train the network to minimize errors in prediction accuracy, by automatically learning features for input values by learning massive data in the deep neural network composed of a multi-layered network.

The above-described deep learning model 221 may be a convolutional neural network (CNN), deep hierarchical network (DHN), convolutional deep belief network (CDBN), deconvolutional deep network (DDN), recurrent neural network (RNN), or generative adversarial network (GAN), but the present invention is not limited thereto, and may use various deep learning models that may be used currently or in the future.

The above-described deep learning model 221 may be implemented through a deep learning framework. The deep learning framework plays a role to provide a library of functions commonly used when developing the deep learning model 221 and to support the system software or hardware platform to be properly used. In this embodiment, the deep learning model 221 may be implemented using any deep learning framework that has been currently disclosed or will be disclosed in the future.

Referring back to FIG. 11, the deep learning model 221 includes a feature extraction part 222 that extracts features for the image by performing convolution and subsampling on the input image and an output part 224 that marks the prognosis chart with the patient's oral cavity condition in the format of text, symbols, or both text and symbols, using the extracted features.

Convolution creates a feature map using a plurality of filters for each area of the medical image in the convolution layer. Subsampling or pooling reduces the size of the feature map in the subsampling layer to extract features for the image that is invariant to a change in position or rotation.

The feature extraction part 222 may repeat convolution and/or subsampling to extract various levels of features from low-level features, such as dots, lines, or planes, to complex, meaningful high-level features, from the medical image.

The deep learning model, e.g., a CNN-based deep learning model, targets optimally training the parameters present in each individual layer in the feature extraction part 222 and the output part 224. In the deep learning model, the order of data determines the initial parameter value.

The deep learning model 221 may apply random sampling (random in data order) and a regulation technique. Random sampling means that the order of the training data learned from the training data set is different.

The regulation technique is a technique that reduces overfitting, in which a deep learning model over-trained with training data including even noise deteriorates test or diagnosis accuracy. The regulation technique may be, e.g., a drop-out technique or a drop-connected technique.

The drop-out technique is a method for performing learning with the probable parameter value designated as 0 for a specific node. The drop-connected technique is a method for performing learning with the connections between nodes dropped. Although the drop-out technique, as the regulation technique, is described below as an example, it may be any current or future technique or algorithm for reducing overfitting.

The deep learning model 221 uses highly flexible nonlinear algorithms. Accordingly, the result values of the deep learning model 221 may exhibit a large deviation. The deviation between the result values of the deep learning models, i.e., output results, may be reduced by ensembling the output results of the deep learning models 221 based on one or more of a majority vote-based ensemble, an unanimity-based ensemble, and an uncertainty-based ensemble.

In other words, in each of the deep learning modules 221, the internal parameters are trained differently depending on the training scheme, e.g., the sampling order and the randomness of the dropout. Even when trained with the same data and the same deep learning models, each deep learning model may exhibit different results. Therefore, use of one deep learning model may lead to a risk of misjudgment. Therefore, the present embodiment may generate various deep learning models and minimize the risk of misjudgment through an ensemble technique.

Figure 12:
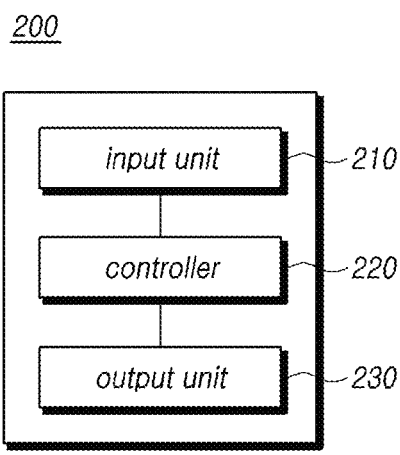
FIG. 12 is a block diagram of a dental medical record device according to another embodiment.

FIG. 12 is a block diagram of a dental medical record device according to another embodiment.

Referring to FIG. 12, a dental medical record device 200 according to another embodiment includes an input unit 210 receiving an image for a patient's oral cavity, a controller 220 reading the image for the patient's oral cavity to determine the patient's oral cavity condition and marking the patient's oral cavity condition on a prognosis chart, using a text format, symbols, or both text and symbols, and an output unit 230 displaying the image and the prognosis chart.

The image may be one of a panoramic photo, a scan image, or a camera image obtained by one or two or more of radiography, oral camera, scanning device, and occlusion check data for the patient's oral cavity.

The patient's oral cavity condition may be at least one of the dental formula, dental conditions, or surrounding structures of the teeth.

The controller 220 may continuously train artificial intelligence with continuously collected training images and accumulated chart data, allowing the artificial intelligence to read the image.

Artificial intelligence may automatically learn the features for input values by being trained with a large amount of data from a deep neural network composed of a multi-layered network, and train the multi-layered network to minimize errors in prediction accuracy and read images.

If a specific treatment site of the image is selected, the display unit 230 displays information about the corresponding treatment site, and if the image of the corresponding treatment site is selected, displays a treatment summary memo window, and if the treatment summary memo window is selected, outputs the chart for the corresponding treatment site.

For example, the controller 220 reads the image shown in FIG. 6 through artificial intelligence and then determines the patient's periodontal condition of alveolar bone loss.

After reading the image shown in FIG. 7A through artificial intelligence, the controller 220 determines the patient's periodontal condition of dental caries.

After reading the image shown in FIG. 7B through artificial intelligence, the controller 220 marks crown in position A, inlay or amalgam in position B, post in position C, and root canal in position D in the step S110 of marking the prognosis chart.

As the information about the treatment site, the display unit 230 displays "Jan. 2, 2020 #44, 45 extractions, 44 immediate implants, receipt: 200,000 won" as shown in FIG. 8A.

As shown in FIG. 8B, if the image of the corresponding treatment site is clicked, the display unit 230 may display a treatment summary memo (e.g., treatment title, date, and receipt) window, and if the treatment summary memo window is clicked, output a chart for the treatment site.

The controller 220 may enhance the accuracy of creating the prognosis chart by continuously learning individually input information or accumulated chart records through artificial intelligence using a machine learning model or a deep learning model.

As described above with reference to FIG. 11, the deep learning model 221 that may be used in the controller 220 may be a model in which the artificial neural networks is composed of multiple layers stacked.

As described above with reference to FIG. 11, the deep learning model 221 includes a feature extraction part 222 and an output part 224. The deep learning model, e.g., a CNN-based deep learning model, targets optimally training the parameters present in each individual layer in the feature extraction part 222 and the output part 224. The deep learning model 221 may apply random sampling (random in data order) and a regulation technique. The deep learning model 221 uses highly flexible nonlinear algorithms.

The above-described dental medical record method 100 may be implemented by a computing device including at least some of a processor, a memory, a user input device, and a presentation device. The memory is a medium that stores computer-readable software, applications, program modules, routines, instructions, and/or data, coded to perform specific tasks when executed by a processor. The processor may read and execute the computer-readable software, applications, program modules, routines, instructions, and/or data stored in the memory. The user input device may be a means for allowing the user to input a command to the processor to execute a specific task or to input data required for the execution of the specific task. The user input device may include a physical or virtual keyboard or keypad, key button, mouse, joystick, trackball, touch-sensitive input means, or a microphone. The presentation device may include, e.g., a display, a printer, a speaker, or a vibrator.

The computing device may include various devices, such as smartphones, tablets, laptops, desktops, servers, clients, and the like. The computing device may be a single stand-alone device and may include a plurality of computing devices operating in a distributed environment composed of a plurality of computing devices cooperating with each other through a communication network.

Further, the above-described dental medical record method 100 may be executed by a computing device that includes a processor and a memory storing computer readable software, applications, program modules, routines, instructions, and/or data structures, coded to perform an image diagnosis method utilizing a deep learning model when executed by the processor.

The present embodiments described above may be implemented through various means. For example, the present embodiments may be implemented by various means, e.g., hardware, firmware, software, or a combination thereof.

When implemented in hardware, the dental medical record method 100 using a deep learning model according to the present embodiments may be implemented by, e.g., one or more application specific integrated circuits (ASICs), digital signal processors (DSPs), digital signal processing devices (DSPDs), programmable logic devices (PLDs), field programmable gate arrays (FPGAs), processors, controllers, micro-controllers, or micro-processors.

For example, the dental medical record method 100 according to embodiments may be implemented by an artificial intelligence semiconductor device in which neurons and synapses of the deep neural network are implemented with semiconductor devices. In this case, the semiconductor devices may be currently available semiconductor devices, e.g., SRAM, DRAM, or NAND or may be next-generation semiconductor devices, such as RRAM, STT MRAM, or PRAM, or may be combinations thereof.

When the dental medical record method 100 according to embodiments is implemented using an artificial intelligence semiconductor device, the results (weights) of training the deep learning model with software may be transferred to synaptic mimic devices disposed in an array, or learning may be performed in the artificial intelligence semiconductor device.

When implemented in firmware or hardware, the dental medical record method 100 according to the present embodiments may be implemented in the form of a device, procedure, or function performing the above-described functions or operations. The software code may be stored in a memory unit and driven by a processor. The memory unit may be positioned inside or outside the processor to exchange data with the processor by various known means.

The above-described terms, such as "system," "processor," "controller," "component," "module," "interface," "model," or "unit," described above may generally refer to computer-related entity hardware, a combination of hardware and software, software, or software being executed. For example, the above-described components may be, but are not limited to, processes driven by a processor, processors, controllers, control processors, entities, execution threads, programs, and/or computers. For example, both an application being executed by a controller or a processor and the controller or the processor may be the components. One or more components may reside within a process and/or thread of execution, and the components may be positioned in one device (e.g., a system, a computing device, etc.) or distributed in two or more devices.

Meanwhile, another embodiment provides a computer program stored in a computer recording medium for performing the above-described dental medical record method 100. Further, another embodiment provides a computer-readable recording medium storing a program for realizing the above-described dental medical record method.

The program recorded on the recording medium may be read, installed, and executed by a computer to execute the above-described steps.

As such, for the computer to read the program recorded on the recording medium and execute the implemented functions with the program, the above-described program may include code coded in a computer language, such as C, C++, JAVA, or machine language, which the processor (CPU) of the computer may read through a computer device interface.

Such code may include a function code related to a function defining the above-described functions or may include an execution procedure-related control code necessary for the processor of the computer to execute the above-described functions according to a predetermined procedure.

Further, the code may further include additional information necessary for the processor of the computer to execute the above-described functions or memory reference-related code as to the position (or address) in the internal or external memory of the computer the media should reference.

Further, when the processor of the computer needs to communicate with, e.g., another computer or a server at a remote site to execute the above-described functions, the code may further include communication-related code as to how the processor of the computer should communicate with the remote computer or server using the communication module of the computer and what information or media should be transmitted/received upon communication.

The above-described computer-readable recording medium may include, e.g., ROMs, RAMs, CD-ROMs, magnetic tapes, floppy disks, or optical data storage devices, or may also include carrier wave-type implementations (e.g., transmissions through the Internet).

Further, the computer-readable recording medium may be distributed to computer systems connected via a network, and computer-readable codes may be stored and executed in a distributed manner.

The functional programs for implementing the present invention and code and code segments related thereto may easily be inferred or changed by programmers of the technical field to which the present invention pertains, considering, e.g., the system environments of the computer reading and executing the program.

The dental medical record method 100 may be implemented in the form of recording media including computer-executable instructions, such as application or program modules. The computer-readable medium may be an available medium that is accessible by a computer. The computer-readable storage medium may include a volatile medium, a non-volatile medium, a separable medium, and/or an inseparable medium. The computer-readable medium may include a computer storage medium. The computer storage medium may include a volatile medium, a non-volatile medium, a separable medium, and/or an inseparable medium that is implemented in any method or scheme to store computer-readable commands, data architecture, program modules, or other data or information.

In a non-transitory computer-readable storage medium storing instructions that, when executed by one or more processors, enable the one or more processors to perform a dental medical record method, the instructions are executed by the one or more processors to enable the computer device to read an image for a patient's oral cavity to mark the patient's oral cavity condition on a prognosis chart, using a text format, symbols, or both text and symbols and display the image and the prognosis chart.

The above-described dental medical record method 100 may be executed by an application installed on a terminal, including a platform equipped in the terminal or a program included in the operating system of the terminal), or may be executed by an application (or program) installed by the user on a master terminal via an application providing server, such as a web server, associated with the service or method, an application, or an application store server. In such a sense, the above-described glaucoma surgery result diagnosis method may be implemented in an application or program installed as default on the terminal or installed directly by the user and may be recorded in a recording medium or storage medium readable by a terminal or computer. Although embodiments of the present invention have been described with reference to the accompanying drawings, It will be appreciated by one of ordinary skill in the art that the present disclosure may be implemented in other various specific forms without changing the essence or technical spirit of the present disclosure. Thus, it should be noted that the above-described embodiments are provided as examples and should not be interpreted as limiting. Each of the components may be separated into two or more units or modules to perform its function(s) or operation(s), and two or more of the components may be integrated into a single unit or module to perform their functions or operations.

It should be noted that the scope of the present invention is defined by the appended claims rather than the described description of the embodiments and include all modifications or changes made to the claims or equivalents of the claims.

CROSS-REFERENCE TO RELATED APPLICATION

The instant patent application claims priority under 35 U.S.C. 119(a) to Korean Patent Application Nos. 10-2020-0004128 and 10-2020-0182812, filed on Jan. 13, 2020 and Dec. 24, 2020, respectively, in the Korean Intellectual Property Office, the disclosures of which are herein incorporated by reference in their entireties. The present patent application claims priority to other applications to be filed in other countries, the disclosures of which are also incorporated by reference herein in their entireties.

The invention claimed is:

1. A dental medical record method comprising:
receiving with a dental medical record device an image of a patient's oral cavity;
reading with a controller of the dental medical record device the image for a patient's oral cavity to mark the patient's oral cavity condition on a prognosis chart, using a text format, symbols, or both text and symbols; and
displaying the image and the prognosis chart on an output unit of the dental medical record device;
wherein the controller reads the image through a deep learning model including a feature extraction part that extracts features for the image by performing convolution and subsampling on the image and an output part that marks the prognosis chart with the patient's oral cavity condition with at least one of text and symbols using the extracted features, and
wherein in the displaying the image and the prognosis chart, the deep learning model is continuously trained with continuously collected training images and accumulated prognosis chart data to read the image wherein the collected training images include a guide chip with a different gray scale or a guide sample including a color number and a color corresponding to the color number, and the oral condition of the patient is indicated on the prognosis chart in text format or by combining the text and the symbol;
wherein in the displaying the image and the prognosis chart, when a specific tooth is clicked on the image, the color of the specific tooth presented by the deep learning model learned on the image is displayed as the color number and color of the guide sample.

2. The dental medical record method of claim 1, wherein the image is one of a panoramic photo, a scan image, or a camera image obtained by one or two or more of radiography, oral camera, scanning device, and occlusion check data for the patient's oral cavity, and
wherein the patient's oral cavity condition is at least one of a dental formula, a dental condition, or a surrounding structure of teeth.

3. The dental medical record method of claim 1, wherein the deep learning model automatically learns features for input values by being trained with a large amount of data from a deep neural network composed of a multi-layered network and train the multi-layered network to minimize errors in prediction accuracy and read the image.

4. The dental medical record method of claim 1, wherein in marking the prognosis chart, if a specific treatment site of the image is selected, information about the corresponding treatment site is displayed, and if the image of the corresponding treatment site is selected, a treatment summary memo window is displayed, and if the treatment summary memo window is selected, the chart for the corresponding treatment site is output.

5. A dental medical record device, comprising:
an input unit receiving an image for a patient's oral cavity;
a controller reading the image for the patient's oral cavity to determine the patient's oral cavity condition and marking the patient's oral cavity condition on a prognosis chart, using a text format, symbols, or both text and symbols; and
an output unit displaying the image and the prognosis chart;
wherein the controller reads the image through a deep learning model including a feature extraction part that extracts features for the image by performing convolution and subsampling on the image and an output part that marks the prognosis chart with the patient's oral cavity condition with at least one of text and symbols using the extracted features, and
wherein in the displaying the image and the prognosis chart, the deep learning model is continuously trained with continuously collected training images and accumulated prognosis chart data to read the image wherein the collected training images include a guide chip with a different gray scale or a guide sample including a color number and a color corresponding to the color number, and the oral condition of the patient is indicated on the prognosis chart by combining the text and the symbol;
wherein when a specific tooth is clicked on the image, the color of the specific tooth presented by the deep learning model learned on the image is displayed as the color number and color of the guide sample.

6. The dental medical record device of claim 5, wherein the image is one of a panoramic photo, a scan image, or a camera image obtained by one or two or more of radiography, oral camera, scanning device, and occlusion check data for the patient's oral cavity, and wherein the patient's oral cavity condition is at least one of a dental formula, a dental condition, or a surrounding structure of teeth.

7. The dental medical record device of claim 5, wherein the deep learning model automatically learns features for input values by being trained with a large amount of data from a deep neural network composed of a multi-layered network and train the multi-layered network to minimize errors in prediction accuracy and read the image.

8. The dental medical record device of claim 5, wherein if a specific treatment site of the image is selected, the display unit displays information about the corresponding treatment site, and if the image of the corresponding treatment site is selected, displays a treatment summary memo window, and if the treatment summary memo window is selected, outputs the chart for the corresponding treatment site.

9. A non-transitory computer-readable storage medium storing instructions that, when executed by one or more controllers, enable the one or more controllers to perform a dental medical record method, the instructions comprising:

receiving with a dental medical record device an image of a patient's oral cavity;

reading with the one or more controllers of the dental medical record device the image for a patient's oral cavity to mark the patient's oral cavity condition on a prognosis chart, using a text format, symbols, or both text and symbols; and displaying the image and the prognosis chart on an output unit of the dental medical record device;

wherein the instructions operate the one or more controllers to read the image through a deep learning model including a feature extraction part that extracts features for the image by performing convolution and subsampling on the image and an output part that marks the prognosis chart with the patient's oral cavity condition with text and symbols using the extracted features;

wherein when a specific tooth is clicked on the image, the color of the specific tooth presented by the deep learning model learned on the image is displayed as the color number and color of the guide sample.

* * * * *